United States Patent [19]

Smith et al.

[11] 4,282,155

[45] Aug. 4, 1981

[54] ANTIHYPERCHOLESTEROLEMIC COMPOUNDS

[75] Inventors: Robert L. Smith; Ta-jyh Lee, both of Lansdale, Pa.

[73] Assignee: Merck & Co., Inc., Rahway, N.J.

[21] Appl. No.: 175,459

[22] Filed: Aug. 5, 1980

Related U.S. Application Data

[63] Continuation-in-part of Ser. No. 118,048, Feb. 4, 1980, abandoned.

[51] Int. Cl.$^3$ .................. C07D 309/30; C07C 59/1
[52] U.S. Cl. ............................. 260/343.5; 562/501; 424/279
[58] Field of Search ................... 260/343.5; 562/501

[56] References Cited

U.S. PATENT DOCUMENTS

| | | | |
|---|---|---|---|
| 3,983,140 | 9/1976 | Endo et al. | 260/343.5 |
| 4,049,495 | 9/1977 | Endo et al. | 195/36 R |
| 4,137,322 | 1/1979 | Endo et al. | 424/273 R |
| 4,231,938 | 11/1980 | Monaghan et al. | 260/343.5 |

OTHER PUBLICATIONS

Singer et al., Proc. Soc. Exper. Biol. Med., 102, 370 (1959).
Hulcher, Arch. Biochem. Biophys. 146, 422 (1971).
Brown et al., J. Chem. Soc., Perkin I, 1165 (1976).
Endo et al., J. Antibiotics XXXii, 852 (1979).
Derwent 15706c/09 (Japanese Patent Appl'n 5009-024, 1-22-80).

*Primary Examiner*—Ethel G. Love
*Attorney, Agent, or Firm*—William H. Nicholson; Mario A. Monaco

[57] ABSTRACT

6(R)-[2-(8'-Etherified-hydroxy-2',6'-dimethylpolyhydronaphthyl-1')-ethyl]-4(R)-hydroxy-3,4,5,6-tetrahydro-2H-pyran-2-ones are prepared from the corresponding 8'-acyloxy compounds, some of which are naturally occurring, by protection of the 4(R)-hydroxyl and the 2-keto group, followed by reductive removal of the 8'-acyloxy group, etherification of the resulting 8'-hydroxyl and removal of the protecting groups. The products inhibit the biosynthesis of cholesterol.

6 Claims, No Drawings

ANTIHYPERCHOLESTEROLEMIC COMPOUNDS

SUMMARY OF THE INVENTION

This is a continuation-in-part of copending application, Ser. No. 118,048, filed Feb. 4, 1980 (now abandoned).

This invention relates to a group of 6(R)-[2-(8'-etherified-hydroxy-2',6'-dimethylpolyhydronaphthyl-1')-ethyl]-4(R)-hydroxy-3,4,5,6-tetrahydro-2-H-pyran-2-ones and to the hydroxy acid form of said pyranones and the salts and esters of said acid form.

More specifically, this invention relates to a compound of the structure $I_{a-e}$ in Table I in which R is:
- $C_{1-18}$ alkyl, straight or branched chain,
- $C_{4-10}$ cycloalkyl,
- $C_{2-10}$ alkenyl,
- $C_{5-10}$ cycloalkenyl,
- $C_{2-10}$ alkynyl,
- phenyl $C_{1-3}$ alkyl,
- substituted phenyl $C_{1-3}$ alkyl in which the substituent is halogen, such as F, Cl, Br, I, CF$_3$ or CN, or
- $C_{1-10}$ alkyl having one or more —O—, —S—, or

in the chain, and in which the dotted lines X, Y and Z represent possible double bonds, said double bonds being, when any are present, either X and Z together in combination or X, Y or Z alone, together with the free hydroxy acids, formed by opening the lactone ring, of the formula $II_{a-e}$ in Table I and the pharmaceutically acceptable salts, the loweralkyl esters and the phenyl, dimethylamino and acetylamino substituted loweralkyl esters of said free hydroxy acids.

BACKGROUND OF THE INVENTION

It is known that certain mevalonate derivatives inhibit the biosynthesis of cholesterol, cf. F. M. Singer et al, *Proc. Soc. Exper. Biol. Med.*, 102, 370 (1959) and F. H. Hulcher, *Arch. Biochem. Biophys.*, 146, 422 (1971). Nevertheless, the activity of these known compounds has not always been found to be satisfactory, i.e. to have practical application.

Recently, Endo et al, reported (U.S. Pat. No. 4,049,495, U.S. Pat. No. 4,137,322 and U.S. Pat. No. 3,983,140) the production of fermentation products which were quite active in the inhibition of cholesterol biosynthesis. This natural product, now called Compactin, was reported by Brown et al (*J. Chem. Soc. Perkin I* 1165 (1976)) to have a complex mevalonolactone structure.

More recently Monaghan et al in U.S. Ser. No. 048,946, filed June 15, 1979, now U.S. Pat. No. 4,231,938, which is incorporated herein by reference, reported an even more potent inhibitor, having the structure $III_a$ in Table I isolated from an entirely different fermentation. Albers-Schonberg et al (U.S. Ser. No. 154,157, filed May 28, 1980) described a dihydro-$III_a$ designated Compound $III_d$ of equal potency isolated from the same fermentation.

Patchett et al (U.S. Ser. No. 118,050, filed Feb. 4, 1980) describe dihydro and tetrahydro derivatives of $III_a$ with structures of Compounds $III_{b,c,e}$ prepared by the catalytic hydrogenation of $III_a$.

The preparation of the starting material, $III_d$, as mentioned previously, is described by Albers-Schonberg et al in U.S. application, Ser. No. 154,157, filed May 28, 1980 and is a product of the following fermentation with a strain of *Aspergillus terreus*, ATCC No. 20542, designated MF-4845 in the culture collection of Merck & Co., Inc., Rahway, N.J.

Preparation of Compound $III_d$

A. Fermentation

A tube of lyophilized culture MF-4845 was opened aseptically and the contents suspended in an unbaffled 250 ml Erlenmeyer flask (seed flask) containing approximately 10 ml of the Medium which has the following composition:

| Medium | |
|---|---|
| Corn steep liquor | 5 g |
| Tomato paste | 40 g |
| Oatmeal | 10 g |
| Glucose | 10 g |
| Trace Element Solution | 10 g |
| Distilled water | 1000 ml |
| pH 6.8 with NaOH | |

| Trace Element Solution: | |
|---|---|
| FeSO$_4$ . 7H$_2$O | 1000 mg |
| MnSO$_4$ . 4H$_2$O | 1000 mg |
| CuCl$_2$ . 2H$_2$O | 25 mg |
| CaCl$_2$ . 2H$_2$O | 100 mg |
| H$_3$BO$_3$ | 56 mg |
| (NH$_4$)$_6$Mo$_7$O$_{24}$ . 4H$_2$O | 19 mg |
| ZnSO$_4$ . 7H$_2$O | 200 mg |
| Distilled Deionized Water | 1000 ml |

The inoculated flask was incubated for 24 hours at 28° C. on a 220 rpm shaker (2 inch throw). An unbaffled 2 liter Erlenmeyer flask containing 500 ml of the medium and then inoculated with 10 ml of the first stage fermentation growth from the seed mixture. This too was shaken 24 hours at 28° C.

A 200 gallon stainless steel fermentation vat was then charged with 485 liters of a medium comprising:

| Cerelose | 4.5% wt/vol |
|---|---|
| Peptonized Milk | 2.5% wt/vol |
| Autolyzed yeast | 0.25% wt/vol |
| Polyglycol P2000 | 0.25% vol/vol | whose pH was adjusted to 7.0. This was sterilized 15 minutes at 121° C. One liter of the second stage above was then charged and the mixture was incubated at 85 rpm for 12 hours then 130 rpm for 84 hours at 28° C. with an air flow of 5 cfm for 12 hours then 10 cfm for 84 hours.

B. Isolation

1. Extraction

Two batches of one hundred gallons of whole broth were combined, acidified with stirring to pH 4.1 by careful addition of 800 ml of concentrated hydrochloric acid, and extracted by addition of 75 gal of ethyl acetate and further stirring for two hours.

About 25 lbs of a silicaceous filter aid was then added and the total slurry was pumped through a 24-inch filter press. An additional 75 gal of ethyl acetate was used to wash the press cake and continue the extraction, by reversing the direction of pumping through the press four times. Then all of the wash solvent was discharged from the press and combined with the first filtrate. The two-phase filtrate was allowed to settle, and the water layer removed. The ethyl acetate layer was washed with 10 gal of deionized water, the phases were allowed to separate and the ethyl acetate extracts were concentrated under vacuum to a residue of about 10 gal.

2. Lactonization

Ethyl acetate extracts from an additional three hundred gal of broth were added to the above extract and the volume was reduced to about thirty gal by vacuum distillation. About fifty gal of toluene was added, and the batch was concentrated under vacuum to 32 gal; this step was repeated; then sufficient new toluene was added to bring the volume to 75 gal. Without vacuum, the batch was brought to reflux and maintained there for two hours, with a temperature over 106° C.

This solution was then concentrated under vacuum to a small volume, which was further concentrated to an oily residue in a large rotary evaporator under vacuum.

3. Chromatography on Silica Gel

The extract obtained above was flushed free of other solvents by addition of 2 gal of methylene chloride and reconcentration to an oil.

The oily residue was dissolved in about 5 gal of ethyl acetate-methylene chloride (30/70; v/v) mixture, and a slurry was made by addition of 2.8 kg of silica gel.

The slurry was loaded as a level layer on the top of a 12 in.×50 in. silica gel column packed in the same solvent mixture.

Elution was with ethyl acetate-methylene chloride (40/60; v/v) at 800 ml/min. A forerun of 10 gal, then further fractions of 4 gal each were collected.

Fractions 6-10 inclusive were concentrated under vacuum to an oily residue which was dissolved in hot ethyl acetate, treated with decolorizing carbon, filtered hot, and cooled. Crystals of Compound $III_a$ were filtered off and the mother liquors were concentrated to an oil for further chromatography.

4. Rechromatography on Silica Gel

Mother liquor residues from similar broth extract work-ups equivalent to an additional 600 gal of fermentation production were combined with the above in methylene chloride solution. One-half of this solution was taken for further silica gel chromatography. A small aliquot showed a total solids content of 325 g. The solution was treated with 40 g of decolorizing carbon, filtered, and the cake rinsed with methylene chloride. The combined filtrate and washings were concentrated under vacuum to an oily residue. This was redissolved in 800 ml of ethyl acetate/methylene chloride (30/70; v/v) and slurried with 225 g of silica gel. The slurry was loaded on top of a 14×36 cm column bed of silica gel packed in the same solvent mixture. Development was with ethyl acetate/methylene chloride (40/60; v/v). A forecut of three liters was set aside; then fractions of 800 ml each were collected.

5. Chromatography on Reverse-phase Packing

Forty ml from fraction 12 of the above chromatogaphy were concentrated to an oil weighing 500 mg and the oil redissolved in 5 ml acetonitrile. This acetonitrile solution was charged to a ⅜" OD by 6 ft long stainless steel chromatography column packed with preparative reverse-phase liquid chromatography column packing material "Bondapak C18/PorasilB" (Waters Associates, Inc., Milford, Mass. 01757). The column was eluted with a mixture consisting of v/v 55% acetonitrile and 45% 0.05 M ammonium phosphate pH 3. The elution volume between 1360 ml and 1700 ml was combined on the basis of refractive index detection. The organic solvent was removed in vacuo and the residual aqueous solution extracted with ethyl acetate. In vacuo removal of the ethyl acetate left 120 mg of compound which crystallized from a concentrated acetonitrile solution yielding crystals of Compound $III_d$, m.p. 129°-131° C.

Starting materials $III_b$, $III_c$ and $III_e$ as mentioned above are described in U.S. application Ser. No. 118,050, filed Feb. 4, 1980 by Patchett et al., in accordance with the following Flow Sheet and preparative methods extracted therefrom.

FLOW SHEET

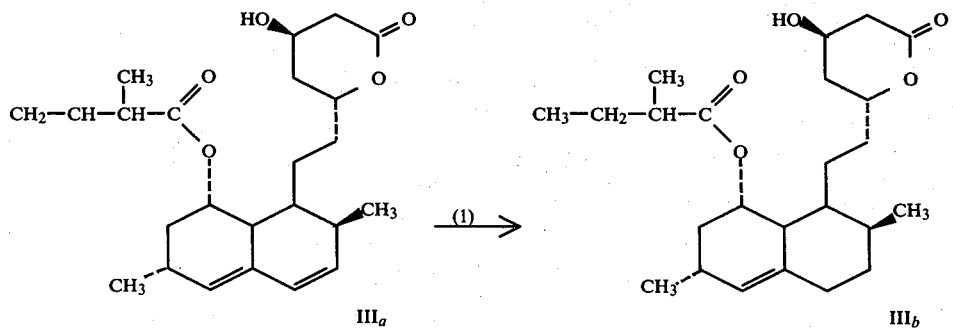

-continued
FLOW SHEET

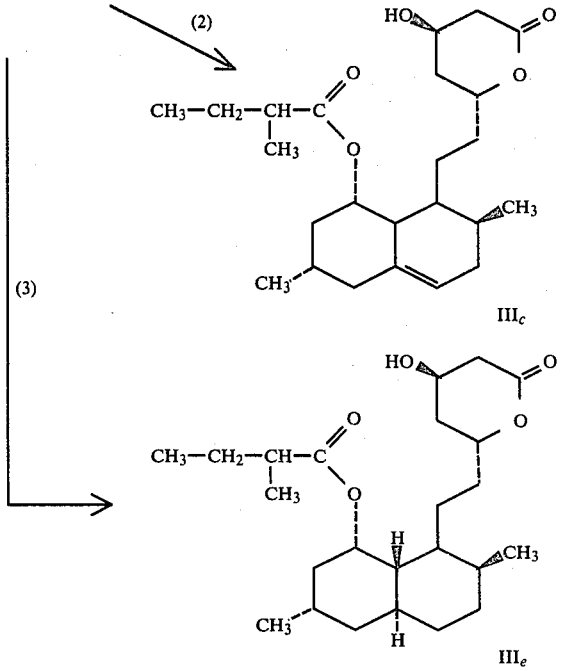

Reactions and Reagents (1) Hydrogenation at room temperature and one atmosphere over tris-(triphenylphosphine)chlororhodium in toluene.

(2) Hydrogenation at room temperature and one atmosphere over 5% palladium on calcium carbonate, in ethanol.

(3) Hydrogenation at room temperature and one atmosphere over platinum oxide in ethyl acetate.

Preparation of 6α[2-(8α-2(S)-methylbutyryloxy-2β,6α-dimethyl-1,2,3,4,6,7,8,8a-octahydronaphthyl-1)ethyl]-4β-hydroxy-3,4,5,6-tetrahydro-2H-pyran-2one, III$_b$ A mixture of 50 mg (0.1236 mmol) of Compound III$_a$ and an equal molar amount (114.35 mg, 0.1236 mmol) of tris-(triphenylphosphine)chlororhodium in 10 ml of dry toluene was hydrogenated at room temperature for 6 days, with a total uptake of 14.6 ml of hydrogen. The mixture was evaporated in vacuo to dryness. The red residue was subjected to preparative thin layer chromatography on silver nitrate impregnated silica plates and was developed twice in 10% ethyl acetate-ether system. The yield of Compound III$_b$ was 22.3 mg.

Mass spectrum (M/e): 406 (m+); 304 (m-102); 286 (m-102-18).

nmr (CDCl$_3$, 300 MHz): δ4.37 (m,1H); 4.60 (m,1H); 5.34 (d of t, J=2.5 Hz, 1H); 5.41 (m,1H).

Preparation of 6α[2-(8α-2-(S)-methylbutyryloxy-2β,6α-dimethyl-1,2,3,5,6,7,8,8a-octahydronaphthyl-1)ethyl]-4β-hydroxy-3,4,5,6-tetrahydro-2H-pyran-2-one, III$_c$ A solution of 80.91 mg (0.2 mmol) of Compound III$_a$ in 10 ml of absolute ethanol, in the presence of an equal weight of 5% Pd on CaCO$_3$ was hydrogenated at 1 atmosphere until an uptake of one mole equivalent of hydrogen was observed. The catalyst was then removed by filtration and the filtrate was evaporated to dryness (81 mg). After a purification by preparative thin-layer chromatography to remove a small amount of by-product tetrahydro compound, 72 mg of the 1,4 reduction product III$_c$ was isolated.

Mass Spectrum (M/e): 406 (m+); 304 (m-102); 286 (304-H$_2$O).

nmr (CDCl$_3$, 300 MHz): δ4.38 (m,1H9; 4.64 (m,1H); 5.28 (d of t, J=3.5 Hz, 1H); 5.48 (m,1H).

Preparation of 6α-[2-(8α-2(S)-methylbutyryloxy-2α,6β-dimethyl-1,2,3,4,4aα,5,6,7,8,8a-decahydronaphthyl-1)ethyl]-4β-hydroxy-3,4,5,6-tetrahydro-2H-pyran-2-one, III$_e$ A solution of 80.91 mg (0.2 mmol) of Compound III$_a$ in 10 ml of ethyl acetate was hydrogenated in the presence of an equal weight of platinum oxide at one atmosphere. An exact 2 mole equivalent of hydrogen was consumed within 1 hour. The catalyst was removed by filtration and the filtrate was concentrated to dryness to give an oil. The cis and trans isomers were separated by preparative thin-layer chromatography on silica gel plates (10% ethyl acetate-ether system, bands detected by water spray). The trans isomer III$_e$ appears as the more polar spot, compared to the cis isomer, and 60 mg was isolated.

Mass spectrum (M/e): 408 (m+); 323 (m-85); 306 (m-102).

nmr (CDCl$_3$, 300 MHz): δ4.36 (broad singlet, 1H); 4.59 (m,1H); 5.19 (d of t, J=2.5 Hz, 1H).

DESCRIPTION OF THE INVENTION

We have found that the 8'-acyloxy group in the polyhydronaphthyl moiety in III$_{a-e}$, described by the various inventors mentioned above, may be converted to 8'-etherified hydroxy derivatives, Compound I$_{a-e}$ which also are potent inhibitors of cholesterol synthesis at the HMG coenzyme A reductase level. More specifically, we have found that compounds of structures I$_{a-e}$ and II$_{a-e}$ are potent antihypercholesterolemic agents, less subject to hydrolysis than the prior compounds. Especially preferred are those in which the etherifying group is a branched chain alkyl, such as isobutyl, a halophenyl-C$_{1-3}$ loweralkyl, such as fluorobenzyl, loweralkenyl, such as allyl, or loweralkynyl, such as propyn-2-yl.

The absolute stereo configuration of these compounds is known from X-ray diffraction. Table I provides a convenient tabulation of these structures and their stereochemical relationship. The reference numerals to the various compounds, including those of the various series of polyhydronaphthyl structures, remain the same throughout these specifications and are so used. Each of the ethers I$_{a-e}$, which comprise this invention contains seven or eight chiral centers. The relative and absolute configuration of these asymmetric centers is as depicted in Table I. More specifically, for ether I$_a$, the Cahn, Ingold, Prelog designations for the absolute configurations are 4(R), 6(R), 1'(S), 2'(S), 6'(R), 8'(S) and 8a'(R) [R. S. Cahn, C. Ingold and V. Prelog, *Ang. Chem. Int. Ed.*, 5, 385 (1966)].

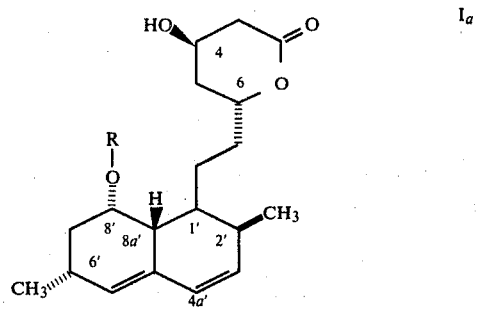

As is indicated in the formulas I$_{a-e}$, all of these compounds have the same spatial orientation of groups at each chiral carbon atom and therefore belong to the same stereochemical series. The R,S designation for each center may not be identical to that found for the ether I$_a$ because of the details of the sequence rules used for determining that designation. In the two ethers I$_d$ and I$_e$ which have an additional chiral carbon atom not present in ether I$_a$, the hydrogen atom at 4a is in the down (or α) orientation as depicted in Table I, giving a trans ring junction.

TABLE I

THE COMPOUNDS OF THIS INVENTION AND THEIR STEREO-RELATIONSHIP

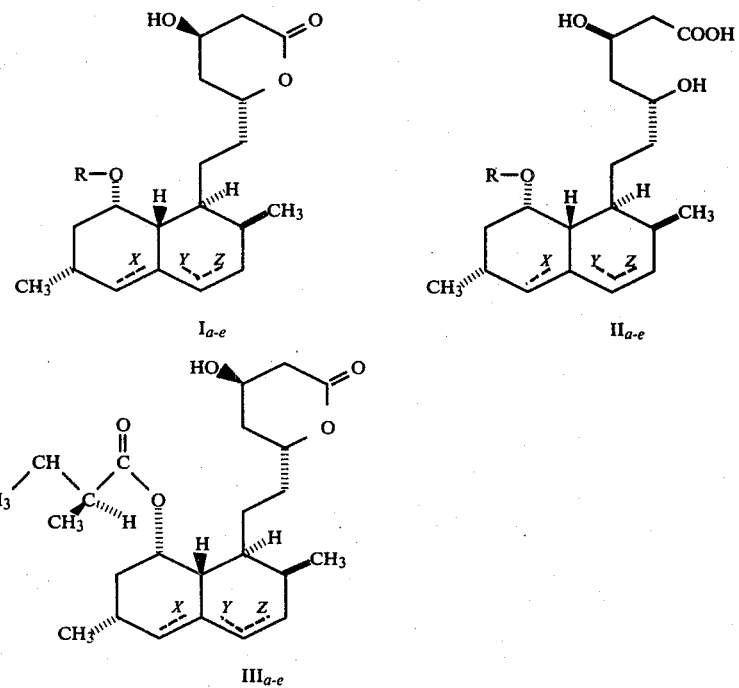

STEREOCHEMISTRY OF THE HYDRONAPHTHYL SERIES

| Series | Double Bonds Present | Structure |
|--------|---------------------|-----------|
| a | X and Z | 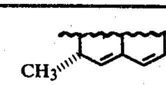 |
| b | X | 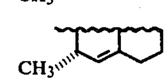 |
| c | Y | 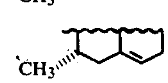 |

TABLE I-continued

| | | |
|---|---|---|
| d | Z | 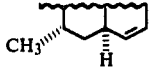 |
| e | None | 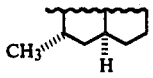 |

The compounds of this invention are highly useful as antihypercholesteremic agents for the treatment of atherosclerosis, hyperlipemia and like diseases in humans. They may be administered orally or parenterally in the form of a capsule, a tablet, an injectable preparation and the like. It is usually desirable to use the oral route. Doses may be varied, depending on the age, severity, body weight and other conditions of human patients but daily dosage for adults is within a range of from about 2 mg to 200 mg (preferably 10 to 100 mg) given in three or four divided doses. Higher doses may be favorably applied as required.

The compounds of this invention also have useful anti-fungal activities. For example, they may be used to control strains of *Penicillium sp. Aspergillus niger, Cladosporium sp., Cochliobolus miyabeanus* and *Helminthosporium cynodnotis*. For those utilities they are admixed with suitable formulating agents, powders, emulsifying agents or solvents such as aqueous ethanol and sprayed or dusted on the plants to be protected.

The preparation of the compounds of this invention is outlined in Flow Sheet A. In summary, it starts with the fixing of a t-butyldimethylsilyl protecting group on the 4(R)-hydroxy of the pyranone ring. This product is then subjected to reduction to convert the keto group in the pyranone ring to an alcohol which is subsequently protected with a tetrahydropyranyl group. This reduction and protection is crucial to the synthesis to prevent loss of the 4-silyloxy protecting group during the subsequent step, which is the removal of the acyl-group from the 8-acyloxy on the polyhydronaphthyl ring with lithium aluminum hydride. The 8-hydroxy group so formed is then etherified by reaction with the appropriate reagent. The 2-hydroxy of the pyran ring is then uncovered and reoxidized to a lactone, after which the silyl group is removed from the 4-hydroxy on the pyranone ring.

FLOW SHEET A

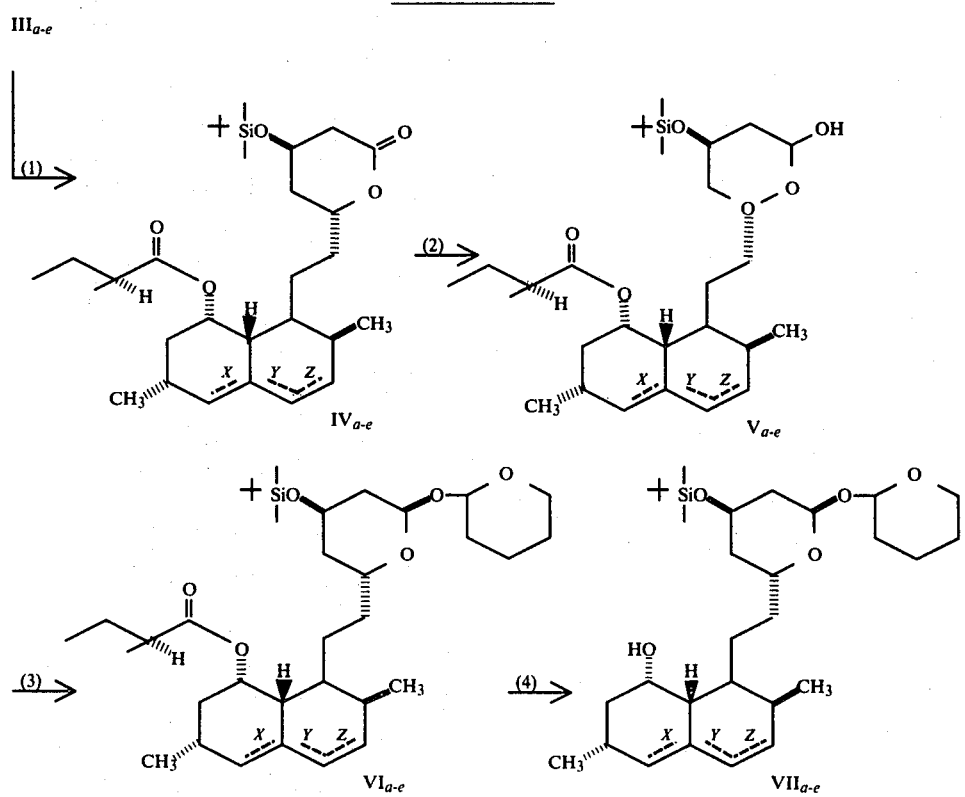

-continued
FLOW SHEET A

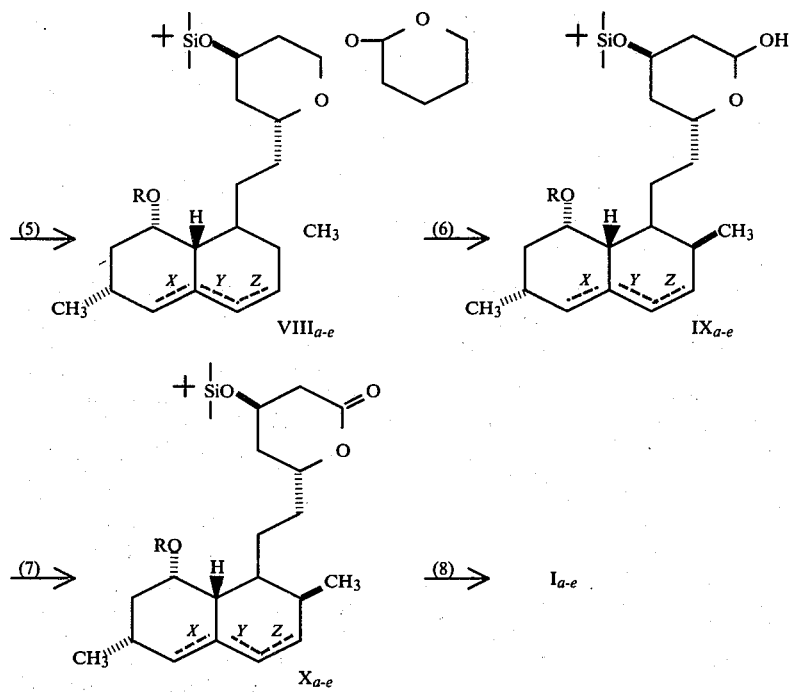

Flow Sheet Definitions

R,X,Y,Z as defined in the specification.

Reactions (1) Stirring with t-butyldimethylchlorosilane in DMF solution in the presence of imidazole catalyst at 0°–50° C.

(2) Low temperature (−100° to −60° C.) reaction with di-isobutylaluminum hydride in THF.

(3) Treatment with dihydropyran and a catalytic amount of pyridinium p-toluenesulfonate in methylene chloride at ambient temperature under an inert atmosphere.

(4) Treating with lithium aluminum hydride in refluxing ether at 0°–40° C. under an inert atmosphere.

(5) Stirring at 0°–90° C. with sodium hydride and R-X (X is a halogen or other removable group).

(6) Stirring in at 10°–30° C. for 40–50 hours with 3 parts of THF to 1 part of acetic acid to one part of water with a catalytic amount of pyridinium p-toluenesulfonate. Time, temperature and ratios are critical to prevent removal of the silyl protecting groups.

(7) Oxidation by silver carbonate on celite in benzene or toluene, at 80°–120° C.

(8) Treatment with 3 equivalents of tetrabutyl ammonium fluoride and four equivalents of acetic acid in THF at ambient temperature under an inert atmosphere.

The invention can be illustrated by the following Examples:

EXAMPLE 1

6(R)-[2-(8′(S)-Methoxy-2′(S),6′(R)-dimethyl-1′,2′,6′,7′,8′,8a′(R)-hexahydronaphthyl-1′(S))-ethyl]-4(R)-hydroxy-3,4,5,6-tetrahydro-2H-pyran-2-one (Compound $I_a$, R=methyl)

A. Preparation of Compound $IV_a$

A solution of t-butyldimethylsilyl chloride (180 mg 1.2 mmoles) in DMF (2.4 ml) is added to a stirred mixture of Compound $III_a$ (300 mg, 0.741 mmol) and imidazole (204 mg, 3 mmol) in DMF (3 ml) while the temperature is maintained at 0° C. The resulting mixture is stirred at room temperature for 16 hours. It is poured into cold water and extracted with ether. The ethereal extract is washed with hydrochloric acid (0.05 N) and aqueous sodium bicarbonate (5%), dried over $MgSO_4$ and filtered. The filtrate is evaporated in vacuo to leave Compound $IV_a$ as a pale yellow, oily residue (0.441 g) which is used directly in the next reaction without further purification: nmr ($CDCl_3$) δ0.08 (6H,s), 0.89 (9H,s), 1.08 (3H,d), 1.10 (3H,d), 2.57 (2H,d), 4.3 (H,m), 4.6 (H,m), 5.4 (H,m), 5.54 (H,m), 5.8 (H,d of d), 6.03 (H,d): $R_f$=0.81 (silica gel, methylene chloride:acetone=9:1).

B. Preparation of Compound $V_a$

A solution of di-i-butylaluminum hydride (1 M in hexane, 0.9 ml) is added via a syringe under a nitrogen atmosphere to a stirred solution of the Compound $IV_a$ prepared above (0.441 g) in THF (15 ml).

During the addition, the temperature is kept at −78° C. The resulting mixture is stirred at −78° C. for 0.5 h. Methanol (0.15 ml) is added and the mixture is stirred for 10 minutes. The cooling bath is removed and water (0.6 ml), celite (0.6 g) and $Na_2SO_4$ (3 g) are added. The resulting mixture is stirred at room temperature for 0.5 h and filtered. The collected solid is washed with ether. The combined filtrate and washings are concentrated at reduced pressure to give Compound $V_a$ as a colorless oil (0.45 g) which is used directly in the subsequent reaction without further purification: nmr (CDCl$_3$) 1.07 (3H,d), 1.10 (3H,d), 3.5~4.2 (2H,m), 4.3 (H,m), 5.1 (H,m), 5.4 (H,m), 5.55 (H,m), 5.8 (H,d of d), 6.05 (H,d); $R_f$=0.48 (silica gel, methylene chloride:acetone=25:1).

C. Preparation of Compound $VI_a$

Dihydropyran (0.6 ml, 6.74 mmoles) is added dropwise to a stirred mixture of Compound $V_a$ (0.45 g) and pyridinium p-toluenesulfonate (20 mg, 0.08 mmol) in methylene chloride (2 ml). The resulting mixture is stirred at room temperature under a nitrogen atmosphere for 16 hours. It is poured into cold water and extracted with ether. The ethereal extract is washed with aqueous sodium bicarbonate, dried over MgSO$_4$ and filtered. The filtrate is concentrated in vacuo to afford an oily residue which is applied to a silica gel column. Elution with methylene chloride:acetone, 50:1(v/v), produces Compound $VI_a$ (0.281 g, 0.46 mmole, 62% overall for Steps A–C) as a colorless, glassy oil:nmr(CDCl$_3$) δ0.07 (6H,S), 0.92(9H,S), 1.07(2H,d), 1.10(2H,d), 3.4~4.1(4H,m), 4.9~5.3(2H,m), 5.4(H,m), 5.55(H,m), 5.8(H,d of d), 6.02(H,d); $R_f$=0.69 (silica gel, methylene chloride: acetone, 25:1).

D. Preparation of Compound $VII_a$

A solution of Compound $VI_a$ (96 mg, 0.159 mmol) in ether (2.5 ml) is added to a stirred suspension of lithium aluminum hydride (35 mg, 0.92 mmol) in ether (3 ml). The resulting mixture is heated at reflux under a nitrogen atmosphere for 15 minutes, then cooled to room temperature and stirred for 16 hours. The reaction mixture is treated successively with water (35 μl), 20% sodium hydroxide (35 μl) and water (105 μl). The resulting mixture is stirred at room temperature for 1 hour and filtered. The filtrate is concentrated to yield an oily residue which is applied to a silica gel column. Elution of the column with methylene chloride: acetone, 50:1(v/v), gives Compound $VII_a$ (58 mg, 0.111 mmol, 70%) as a colorless, glassy oil:nmr(CDCl$_3$) δ0.065(6H,s), 0.90 (9H,s), 1.20(3H,d), 3.3~4.4(5H,m), 4.9~5.3(2H,m), 5.57(H,m), 5.8(H,d of d), 6.08(H,d); $R_f$=0.33 (silica gel, methylene chloride:acetone, 50:1).

E. Preparation of Compound $VIII_a$ (R=methyl)

To a stirred suspension of sodium hydride (50% oil dispersion, 38 mg, 0.75 mmol, washed with petroleum ether prior to use) in DMF (1 ml) is added a solution of Compound $VII_a$ (44 mg, 0.084 mmol) in DMF (1 ml) at room temperature under a nitrogen atmosphere. The resulting mixture is heated on a steam bath for 10 minutes and cooled to room temperature. Methyl iodide (0.1 ml, 1.6 mmol) is added and the resulting reaction mixture is heated on a steam bath for 10 minutes. The mixture is cooled to room temperature, poured into cold water and extracted with ether. The ethereal extract is washed with dilute hydrochloric acid and aqueous sodium bicarbonate, dried over MgSO$_4$ and filtered. The filtrate is evaporated to leave an oily residue which is applied to a silica gel column. Elution with methylene chloride:acetone, 50:1(v/v), affords Compound $VIII_a$ (R=methyl), (29 mg, 0.054 mmole, 65%) as a colorless glassy oil: nmr (CDCl$_3$) δ0.070(6H,s), 0.90(9H,s), 1.15(3H,d), 3.34(3H,s), 3.4~4.1(4H,m), 4.26(H,m), 4.9~5.3(2H,m), 5.5(H,m), 5.75(H,d of d), 6.0(H,d); $R_f$=0.37, 0.40 (silica gel, methylene chloride:acetone, 50:1).

F. Preparation of Compound $IX_a$ (R=methyl)

Powdered pyridinium p-toluenesulfonic (20 mg, 0.08 mmole) is added in one portion to a stirred mixture of Compound $VIII_a$ from part E (82 mg, 0.153 mmole) in THF (2 ml), acetic acid (0.8 ml) and water (0.6 ml). The resulting mixture is stirred at room temperature under a nitrogen atmosphere for 36 hours. The reaction mixture is poured into cold water and extracted with ether. The ethereal extract is washed with water and aqueous sodium bicarbonate and dried over MgSO$_4$ and filtered. The filtrate is concentrated in vacuo to provide an oily residue which is subsequently applied to a silica column. Elution of the column with methylene chloride:acetone, 50:1(v/v), first gives the starting tetrahydropyranyl ether (26 mg, 0.049 mmole). Continued elution with the same eluant produces Compound $IX_a$ (R=methyl) (23 mg, 0.051 mmole, 49% based on consumed starting material) as a colorless glassy oil: nmr (CDCl$_3$) δ1.14(3H,d), 3.34(3H,s), 3.6~4.4(3H,m), 5.0~5.3(H,m), 5.55(H,m), 5.80(H,d of d), 6.00(H,d); $R_f$=0.23(silica gel, methylene chloride:acetone, 50:1).

G. Preparation of Compound $X_a$ (R=methyl)

A mixture of Compound $IX_a$ from part F (23 mg, 0.051 mmole) and freshly prepared silver carbonate/celite (1.6 g) in benzene (7.5 ml) is heated at reflux under a nitrogen atmosphere for 0.5 h. The reaction mixture is cooled to room temperature. The insoluble solid is collected and washed with ether. The combined filtrate and washings are evaporated on a rotary evaporator to leave Compound $X_a$ (R=methyl) (24 mg) as a glassy oil which is used directly in the next step without further purification; nmr(CDCl$_3$) δ0.080(6H,s), 0.90(9H,s), 1.12(3H,d), 2.58(2H,d), 3.33(3H,s), 3.7 (H,m), 4.3(H,m), 4.7(H,m), 5.5(H,m), 5.74(H,d of d), 5.97(H,d); $R_f$=0.41 (silica gel, methylene chloride:acetone, 50:1).

H. Preparation of Compound $I_a$ (R=methyl)

A solution of tetrabutylammonium fluoride trihydrate (0.32 M in THF, 0.75 ml, 0.24 mmole) is added to a stirred mixture of Compound $X_a$ from part G (24 mg) in THF (3 ml) and acetic acid (25 μl, 0.44 mmole). The resulting mixture is stirred at room temperature under a nitrogen atmosphere for 44 hours. The reaction mixture is poured into cold water and extracted with ether. The ethereal extract is washed with aqueous sodium bicarbonate, dried over MgSO$_4$ and filtered. The filtrate is evaporated in vacuo to yield an oily residue which is applied to a silica gel column. Elution with methylene chloride;acetone, 9:1(v/v), provides Compound $I_a$ (R=methyl) (17 mg, 0.051 mmole, 100% overall for the last two steps) as a colorless, glassy oil. This oil solidifies on standing at room temperature and is recrystallized from ether-hexane to afford the pure title compound; mp 110°–111° C.; $R_f$=0.19 (silica gel, methylene chloride:acetone, 9:1; nmr(CDCl$_3$) δ0.87(3H,d), 1.08(3H,d), 2.66(2H,m), 3.34(3H,s), 3.7(H,m), 4.37(H,m), 4.7(H,m), 5.5(H,m), 5.74(H,d of d), 5.97(H,d).

Anal. Calcd. for $C_{20}H_{30}O_4$: C, 71.82; H, 9.04 Found: C, 72.03; H, 9.05.

EXAMPLE 2

Preparation of
6(R)-[2-(8′(S)-4‴-fluorobenzyloxy-2′(S),6′(R)-dimethyl-1′,2′,6′,7′,8′,8a′(R)-hexahydronaphthyl-1′(S))ethyl]-4(R)-hydroxy-3,4,5,6-tetrahydro-2H-pyran-2-one
(Compound $I_a$ when R=p-fluorobenzyl)

By following the same procedures described in Example 1, Steps E–H, but using an equivalent amount of 4-fluorobenzyl chloride instead of methyl iodide, there are obtained successively:

E. Compound $VIII_a$ (R=p-fluorobenzyl)

$R_f$=0.51, 0.57 (silica gel, methylene chloride:acetone, 50:1);
nmr(CDCl₃) δ1.15(3H,d), 4.27(H,d,J=12 Hz), 4.70 (H,d,J=12 Hz), 5.5(H,m), 5.73 (H,d of d), 6.0(H,d), 6.98 (2H,m), 7.28(2H,m).

F. Compound $IX_a$ (R=p-fluorobenzyl)

$R_f$=0.18 (silica gel, methylene chloride: acetone, 100:1);
nmr(CDCl₃) δ1.15(3H,d), 4.30(H,d,J=12 Hz), 4.75 (H,d,J=12 Hz), 5.5(H,m), 5.8(H,d of d), 6.0(H,d), 7.0(2H,m), 7.32(2H,m).

G. Preparation of Compound $X_a$ (R=p-fluorobenzyl)

$R_f$=0.28 (silica gel, methylene chloride:acetone, 100:1);
nmr(CDCl₃) δ1.16 (3H,d), 2.52(2H,d), 3.97(H,m), 4.30(H,d, J=12 Hz), 4.72(H,d,J=12 Hz), 5.52(H,m), 5.75(H,d of d), 6.0(H,d), 7.0(2H,d), 7.3(2H,m).

H. Preparation of Compound $I_a$ (R=p-fluorobenzyl)

$R_f$=0.30 (silica gel, methylene chloride:acetone, 10:1);
nmr(CDCl₃) δ0.86(3H,d), 1.17(3H,d), 2.59(2H,m), 3.90(H,m), 4.30(H,d,J=12 Hz), 4.71(H,d,J=12 Hz), 5.53(H,m), 5.76(H, d of d), 6.01(H,d), 7.03(2H,t), 7.33(2H,m).

EXAMPLE 3

The procedure of Example 1, Step E is followed using an equivalent quantity of the following halides in place of methyl iodide. The product is then taken successively through the procedures of Steps F, G and H of Example 1 to yield the corresponding 6(R)-[2-(8′(S)—RO—2′(S),6′(R)-dimethyl-1′,2′,6′,7′,8′,8a′(R)-hexahydronaphthyl-1′(S))-ethyl]-4(R)-hydroxy-3,4,5,6-tetrahydro-2H-pyran-2-one:

| Halide | RO = |
|---|---|
| n-butyliodide | n-butyloxy- |
| 3-methylpentyliodide | 3″-methylpentyloxy- |
| cyclohexylbromide | cyclohexyloxy- |
| 2-cyclohexenylbromide | 2″-cyclohexeneyloxy |
| 2-butynylbromide | 2″-butynyloxy |
| benzylchloride | benzyloxy- |
| chloromethyl methyl ether | methoxymethoxy- |
| chloromethyl methyl sulfide | methylthiomethoxy- |
| 3-N-methyl-acetamide-propyl iodide | 3″-N-methylacetamido-propyloxy- |
| allyl bromide | 2″-propenyloxy- |
| 2-methyl-2-propenyl bromide | 2″-methyl-2″-propenyloxy |

EXAMPLE 4

A. The procedure of Example 1A is followed using Compounds $III_b$, $III_c$, $III_d$ and $III_e$ in place of Compound $III_a$. The products are then successively taken through the procedures of parts B,C,D,E,F,G and H to yield Compounds $I_b$, $I_c$, $I_d$ and $I_e$ in which R is methyl.

B. The halides used in Example 3 are used in the procedure of Step E instead of methyliodide and the product is likewise taken through the succeeding steps to yield the products in which RO is the various groups listed in Example 3.

EXAMPLE 5

Preparation of the hydroxy acid $II_a$ and its sodium salt corresponding to the lactone $I_a$ of Example 1

To a solution of $10^{-4}$ mole of the Compound $I_a$ in 2 ml of ethanol is added 1 ml of aqueous NaOH ($10^{-4}$ moles; 1 equivalent). After one hour at room temperature, the mixture is taken to dryness in vacuo to yield the sodium salt of Compound $II_a$.

The sodium salt is redissolved in 2 ml of ethanol-water (1:1) and added to 10 ml of 0.1 N hydrochloric acid from which the liberated hydroxy acid is extracted with ethyl acetate. The latter solvent is washed once with water, dried and removed in vacuo with a bath temperature not exceeding 30°. The hydroxy acid slowly reverts to the lactone on standing.

The other hydroxy acids $II_{b-e}$ and their salts are prepared substantially as described in Example 5 from the appropriate lactone $I_{b-e}$.

What is claimed is:

1. A compound of the structure:

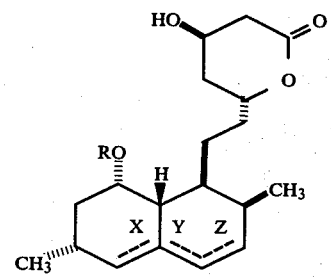

in which R is:
C₁₋₁₈ alkyl, straight or branched chain,
C₄₋₁₀ cycloalkyl,
C₂₋₁₀ alkenyl,
C₅₋₁₀ cycloalkenyl,
C₂₋₁₀ alkynyl,
phenyl C₁₋₃ alkyl,
substituted phenyl C₁₋₃ alkyl in which the substituent is halogen, CF₃ or CN, and
C₁₋₁₀ alkyl having one or more —O—, —S—, or

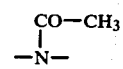

in the chain, in which the dotted lines at X,Y and Z represent possible double bonds, said double bonds, when any are present, being either X and Z in combination or X, Y or Z alone, and the corresponding hydroxy acids of the formula:

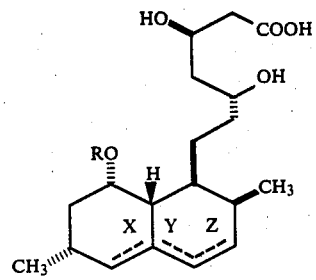

and the pharmaceutically acceptable salts, the loweralkyl esters and the phenyl, dimethylamino and acetylamino substituted loweralkyl esters of said hydroxy acids.

2. A compound of claim 1 in the lactone form.

3. A compound of claim 1 in the free hydroxy acid form or the salts or esters thereof.

4. A compound of claim 2 in which X and Z are double bonds.

5. A compound of claim 4 in which R is methyl.

6. A compound of claim 4 in which R is p-fluorobenzyl.

* * * * *